US012746563B2

(12) United States Patent
Katsuda et al.

(10) Patent No.: US 12,746,563 B2
(45) Date of Patent: Sep. 29, 2026

(54) LIQUID SPRAY NOZZLE AND LIQUID SPRAY DEVICE

(71) Applicant: SEIKO EPSON CORPORATION, Tokyo (JP)

(72) Inventors: Osamu Katsuda, Matsumoto (JP); Kaname Nagatani, Matsumoto (JP); Takahiro Matsuzaki, Shiojiri (JP); Yasunori Onishi, Shiojiri (JP); Tomoki Abe, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 1169 days.

(21) Appl. No.: 17/659,372

(22) Filed: Apr. 15, 2022

(65) Prior Publication Data

US 2022/0331828 A1 Oct. 20, 2022

(30) Foreign Application Priority Data

Apr. 16, 2021 (JP) ................................ 2021-069525

(51) Int. Cl.

*B05B 15/40* (2018.01)
*A61L 2/10* (2006.01)
*B05B 15/50* (2018.01)

(52) U.S. Cl.

CPC ................ *B05B 15/40* (2018.02); *A61L 2/10* (2013.01); *B05B 15/50* (2018.02); *A61L 2202/11* (2013.01)

(58) Field of Classification Search

CPC .. B05B 1/02; B05B 1/14; B05B 15/40; B05B 15/50; B05B 15/58; A61L 2202/11
USPC ......... 239/104, 575, 590, 590.3, 591, 102.1; 604/265
See application file for complete search history.

(56) References Cited

U.S. PATENT DOCUMENTS

| | | | | |
|---|---|---|---|---|
| 6,234,365 | B1 * | 5/2001 | Bougamont | A61M 11/06 239/575 |
| 2010/0222752 | A1 * | 9/2010 | Collins, Jr. | B05B 17/0623 604/296 |
| 2017/0143585 | A1 | 5/2017 | Suzuki et al. | |
| 2020/0216335 | A1 | 7/2020 | Oh | |
| 2023/0311149 | A1 * | 10/2023 | Mock | B05B 1/18 239/104 |

FOREIGN PATENT DOCUMENTS

| | | |
|---|---|---|
| JP | 2017099868 A | 6/2017 |
| JP | 2020110570 A | 7/2020 |

* cited by examiner

*Primary Examiner* — Steven J Ganey
(74) *Attorney, Agent, or Firm* — CHIP LAW GROUP

(57) ABSTRACT

A liquid spray nozzle includes a nozzle hole configured to spray a liquid toward an object, a liquid flow channel communicated with the nozzle hole, and a filter disposed in the liquid flow channel, wherein at least one of a part of the filter and a part of the liquid flow channel from the filter to the nozzle hole forms an antibacterial part.

6 Claims, 16 Drawing Sheets

LIQUID SPRAY NOZZLE AND LIQUID SPRAY DEVICE

The present application is based on, and claims priority from JP Application Serial Number 2021-069525, filed Apr. 16, 2021, the disclosure of which is hereby incorporated by reference herein in its entirety.

BACKGROUND

1. Technical Field

The present disclosure relates to a liquid spray nozzle and a liquid spray device.

2. Related Art

In the past, there has been used a liquid spray nozzle for spraying a liquid from a nozzle hole toward an object. For example, in JP-A-2017-99868 (Document 1), there is disclosed beauty equipment capable of ejecting an alkali fluid from an alkali fluid ejection port. The beauty equipment in Document 1 is an example of the liquid spray nozzle for spraying a liquid from the nozzle hole toward the object, but as described above, a variety of configurations can be adopted as the liquid spray nozzle for spraying the liquid from the nozzle hole toward the object.

In the liquid spray nozzle for spraying the liquid from the nozzle hole toward the object such as the beauty equipment in Document 1, there is a possibility that a bacterium such as a fungus enters a liquid flow channel from the nozzle hole, the bacterium propagates in the liquid flow channel in the vicinity of the nozzle hole to plug up the nozzle hole, and a spray failure such as a decrease in spray amount of the liquid occurs. Therefore, the present disclosure has an advantage of preventing a bacterium from propagating in the liquid flow channel in the vicinity of the nozzle hole to plug up the nozzle hole to thereby cause the spray failure in the liquid spray nozzle for spraying the liquid from the nozzle hole.

SUMMARY

In view of the problems described above, a liquid spray nozzle according the present disclosure includes a nozzle hole configured to spray a liquid toward an object, a liquid flow channel communicated with the nozzle hole, and a filter disposed in the liquid flow channel, wherein at least a part of the filter and the liquid flow channel from the filter to the nozzle hole forms an antibacterial part.

DESCRIPTION OF AN EXEMPLARY EMBODIMENT

Figure 1:
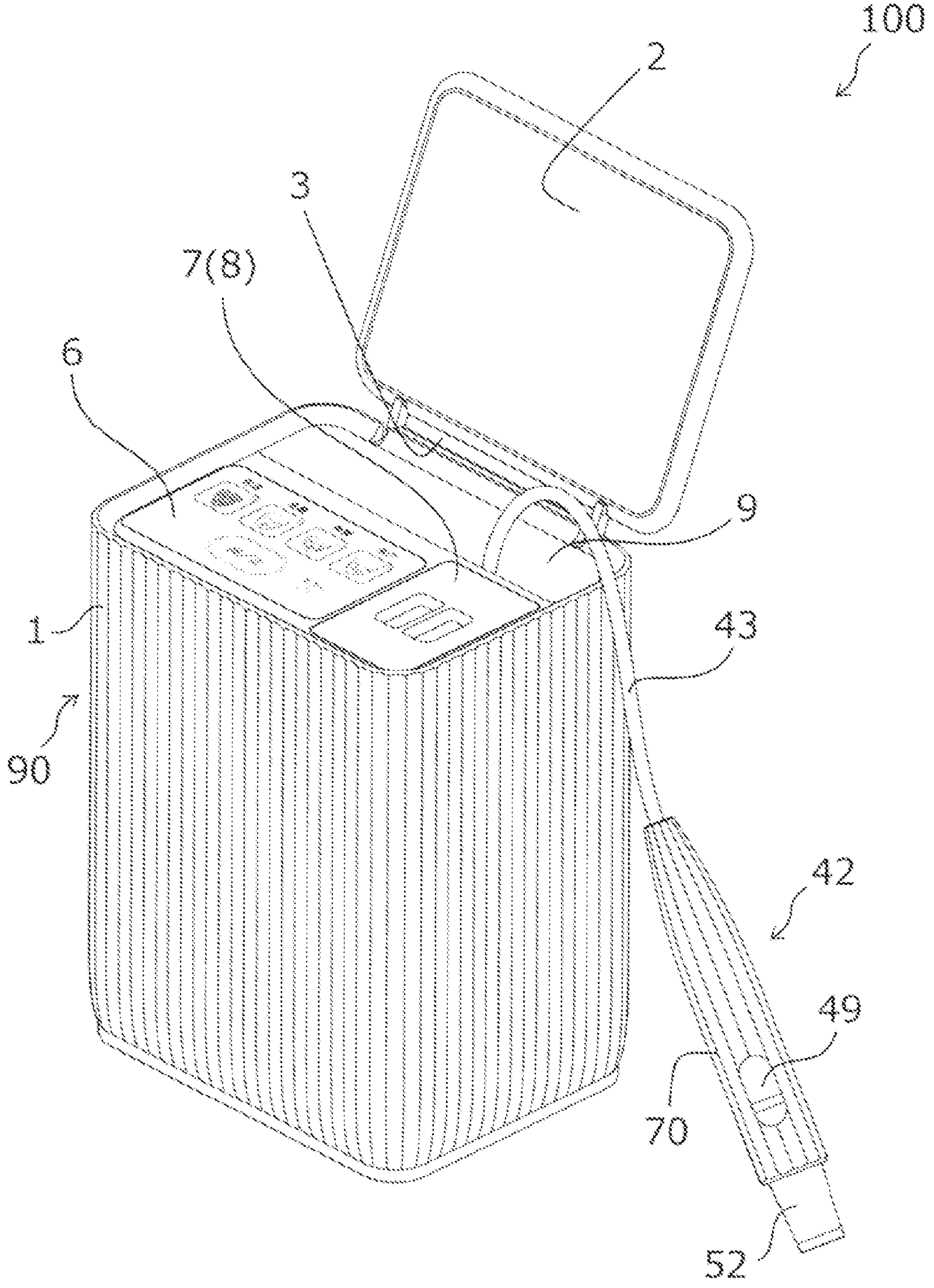
FIG. 1 is a schematic diagram of the whole of a liquid spray device having a liquid spray nozzle according to Practical Example 1 of the present disclosure.
Figure 2:
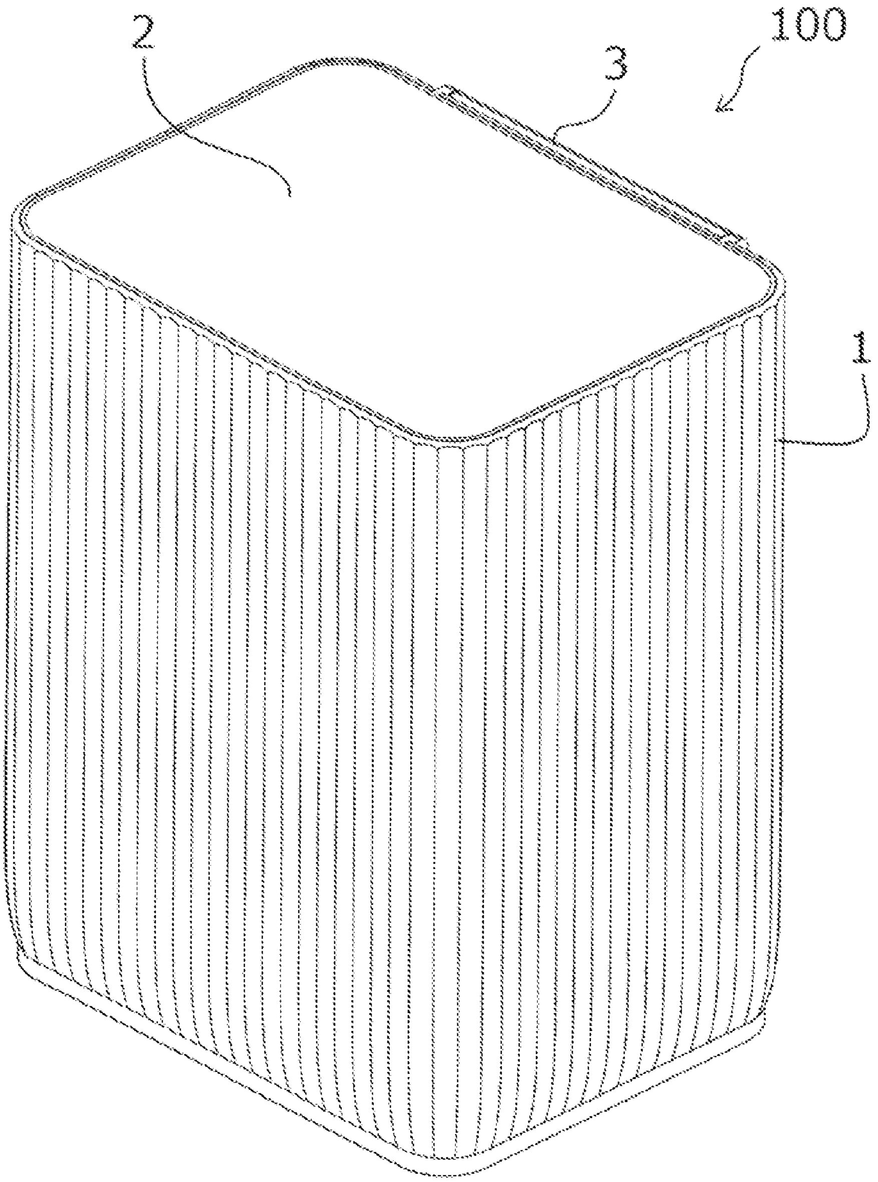
FIG. 2 is a schematic perspective view from a front side of the liquid spray device shown in FIG. 1, and shows a state in which a lid is closed.
Figure 3:
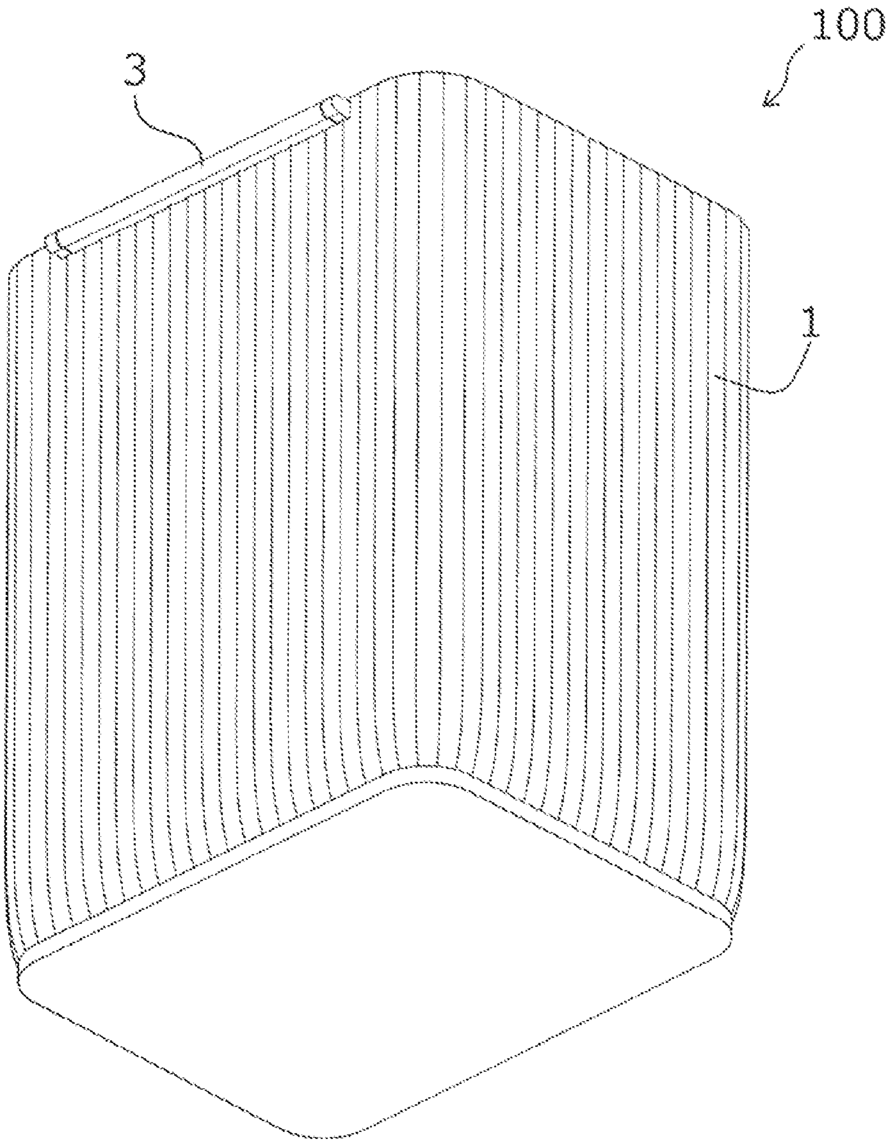
FIG. 3 is a schematic perspective view from a back side of the liquid spray device shown in FIG. 1.

First, the present disclosure will schematically be described.

In view of the problem described above, a liquid spray nozzle according a first aspect of the present disclosure includes a nozzle hole configured to spray a liquid toward an object, a liquid flow channel communicated with the nozzle hole, and a filter disposed in the liquid flow channel, wherein at least a part of the filter and the liquid flow channel from the filter to the nozzle hole forms an antibacterial part.

According to the present aspect, at least a part of the filter and the liquid flow channel from the filter to the nozzle hole forms the antibacterial part. Therefore, it is possible to prevent a bacterium from propagating in the flow channel in the vicinity of the nozzle hole. Therefore, it is possible to prevent the nozzle from being plugged up to cause the spray failure.

In a liquid spray nozzle of a second aspect of the present disclosure according to the first aspect, at least a part of the filter is formed of an antibacterial member as the antibacterial part.

According to the present aspect, at least a part of the filter is formed of the antibacterial member as the antibacterial part. Therefore, it is possible to prevent a bacterium from propagating in the flow channel in the vicinity of the nozzle hole using the filter as the antibacterial part.

In a liquid spray nozzle of a third aspect of the present disclosure according to the first or second aspect, at least a part of the liquid flow channel from the filter to the nozzle hole is formed of an antibacterial member as the antibacterial part.

According to the present aspect, at least a part of the liquid flow channel from the filter to the nozzle hole is formed of the antibacterial member as the antibacterial part. Therefore, it is possible to prevent a bacterium from propagating in the flow channel in the vicinity of the nozzle hole using the liquid flow channel as the antibacterial part.

In a liquid spray nozzle of a fourth aspect of the present disclosure according to any one of the first through third aspects, there is further included a filter holding part configured to hold the filter in the liquid flow channel, wherein at least a part of the filter holding part is formed of an antibacterial member as the antibacterial part.

According to the present aspect, at least a part of the filter holding part is formed of the antibacterial member as the antibacterial part. Therefore, it is possible to prevent a bacterium from propagating in the flow channel in the vicinity of the nozzle hole using the filter holding part as the antibacterial part.

In a liquid spray nozzle of a fifth aspect of the present disclosure according to any one of the first through fourth aspects, there is further included a light emitter as the antibacterial part.

According to the present aspect, the light emitter is provided as the antibacterial part. Therefore, it is possible to prevent a bacterium from propagating in the flow channel in the vicinity of the nozzle hole using the light emitter as the antibacterial part.

A liquid spray device according to a sixth aspect of the present disclosure includes the liquid spray nozzle according to any one of the first through fifth aspects, and a liquid supply device configured to supply the liquid spray nozzle with the liquid.

According to the present aspect, at least a part of the filter and the liquid flow channel from the filter to the nozzle hole forms the antibacterial part. Therefore, it is possible to prevent a bacterium from propagating in the flow channel in the vicinity of the nozzle hole. Therefore, it is possible to prevent the nozzle from being plugged up to cause the spray failure.

Practical Example 1

An embodiment according to the present disclosure will hereinafter be described with reference to the accompanying drawings. Here, a liquid spray device 100 is described as a droplet-impact pressure facial cleanser to a facial skin and so on. It should be noted that it is obvious that the liquid spray device 100 is not limited to one for the facial skin, the liquid spray device 100 can be applied to washing of a skin of, for example, arms, hands, legs, and a back, and can further be applied to washing of an object other than a living body.

First, an outline of the liquid spray device 100 according to the present practical example will be described with reference to FIG. 1 through FIG. 5. The liquid spray device 100 according to the present practical example is for washing the skin of a face or the like with a liquid sprayed from a hand piece 42 as a spray nozzle. Specifically, as shown in FIG. 1, the liquid spray device 100 according to the present practical example is provided with the hand piece 42 for spraying the liquid, and a liquid supply device 90.

As shown in FIG. 1, the liquid supply device 90 is provided with a case 1, a lid 2, an operation panel 6, a tank 7 for retaining the liquid to be sprayed, and a liquid delivery tube 43 for communicating the tank 7 and the hand piece 42 with each other. It should be noted that in FIG. 1, out of the tank 7, only a tank lid 8 is viewed. The lid 2 can be displaced to an open state shown in FIG. 1 and a closed state shown in FIG. 2 and FIG. 3 by being rotated with reference to a hinge 3. It should be noted that inside the liquid supply device 90, there is disposed a pump which is not shown in FIG. 1 through FIG. 5, and there is adopted a configuration in which the liquid can be supplied to the hand piece 42 from the tank 7 via the liquid delivery tube 43 due to the pressure by the pump. The hand piece 42 can be housed in a hand piece housing section 9.

Figure 4:
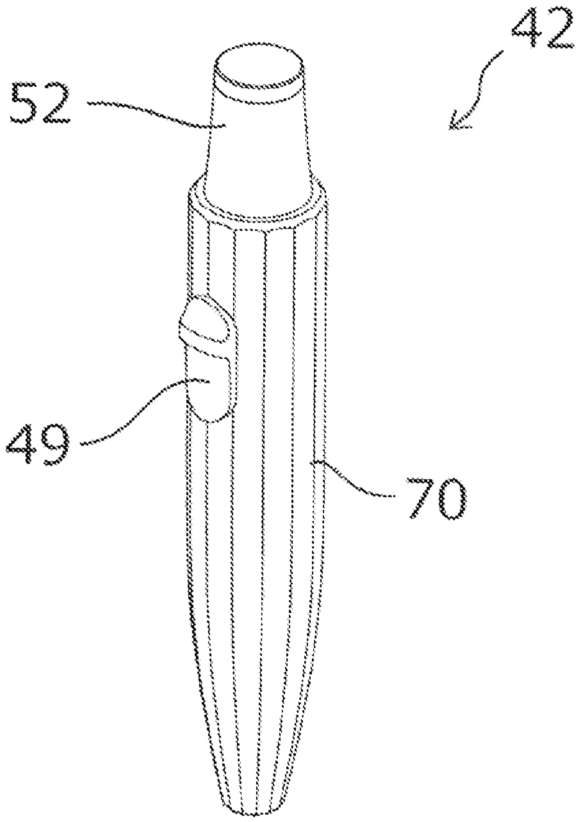
FIG. 4 is a schematic perspective view of the liquid spray nozzle in the liquid spray device shown in FIG. 1.
Figure 5:
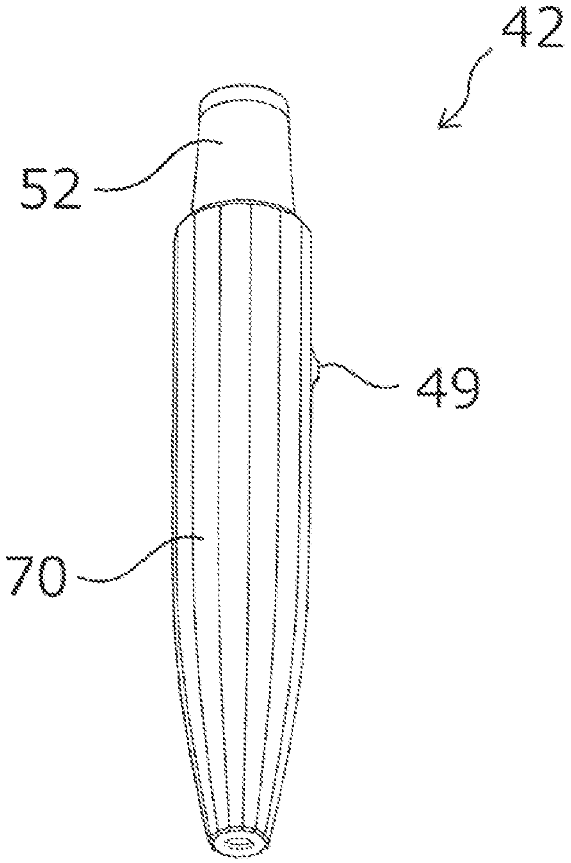
FIG. 5 is a schematic perspective view of the liquid spray nozzle in the liquid spray device shown in FIG. 1, and is a diagram viewed from a direction different from a direction from which the schematic perspective view of FIG. 4 is viewed.

As shown in FIG. 1, FIG. 4, and FIG. 5, the hand piece 42 is provided with a main body unit 70 and a tip cap 52. The main body unit 70 is provided with a valve opening and closing switch 49, and the liquid is sprayed from the hand piece 42 by the user setting the valve opening and closing switch 49 to the ON state, and the spray of the liquid from the hand piece 42 is stopped by the user setting the valve opening and closing switch to the OFF state.

Figure 6:
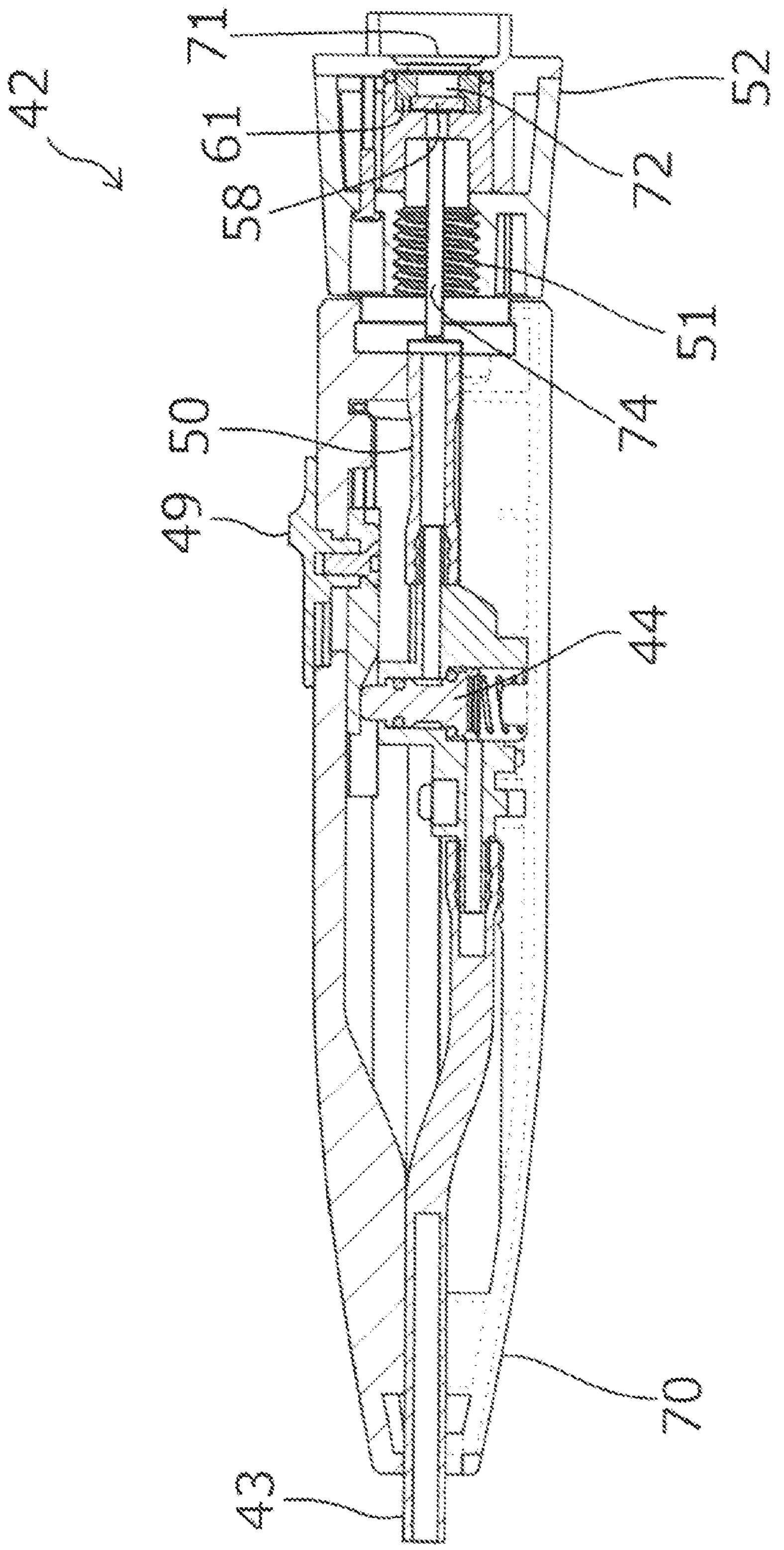
FIG. 6 is a cross-sectional view of the liquid spray nozzle according to Practical Example 1 of the present disclosure.
Figure 7:
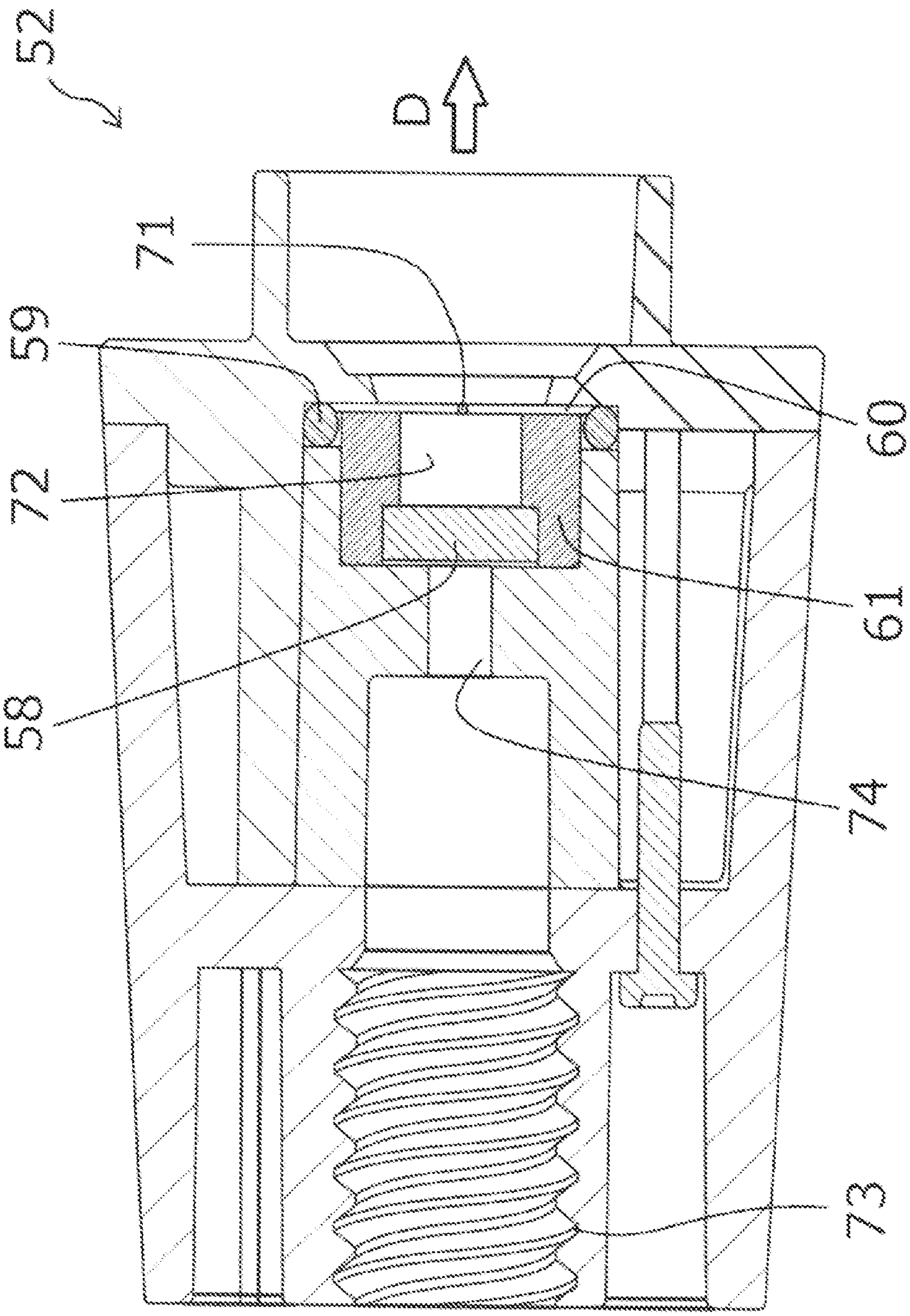
FIG. 7 is a cross-sectional view of a nozzle unit of the liquid spray nozzle according to Practical Example 1 of the present disclosure.

Then, the details of the hand piece 42 in the present practical example will be described in detail with reference to FIG. 6 and FIG. 7. As shown in FIG. 6, the tip cap 52 is attached to a tip of the main body unit 70. Specifically, as shown in FIG. 6, at the tip of the main body unit 70, there is disposed a tip cap connector 51 as an external thread part provided with a liquid flow channel 74 formed inside. Further, as shown in FIG. 7, the tip cap 52 is provided with an internal thread part 73, and by engaging the tip cap connector 51 with the internal thread part 73, the tip cap 52 is attached to the tip of the main body unit 70. Here, the tip means a tip in a spray direction D of the liquid shown in FIG. 7. It should be noted that in the present practical example, there is adopted the configuration in which the tip cap 52 is attached to the main body unit 70 by engaging the tip cap connector 51 with the internal thread part 73, such a configuration is not a limitation, and it is possible to adopt, for example, a snap-fit configuration in which a protruding part and a recessed part are provided respectively to the tip cap 52 and the main body unit 70, and the protruding part is caught on the recessed part.

Here, as shown in FIG. 6, the main body unit 70 has a valve ASSY 44 to be communicated with the liquid delivery tube 43 in the inside thereof, and the valve ASSY 44 is coupled to the tip cap connector 51 with a coupling tube 50. In other words, the liquid flow channel 74 is formed inside the main body unit 70 from a rear end to the tip. The valve ASSY 44 opens the liquid flow channel 74 in response to the user setting the valve opening and closing switch 49 to the ON state, and closes the liquid flow channel 74 in response to the user setting the valve opening and closing switch 49 to the OFF state.

Further, as shown in FIG. 7, in the liquid flow channel 74 in the tip cap 52, there are disposed a filter 58, a filter holder 61, and a nozzle plate 60. The nozzle plate 60 is arranged so as to have contact with a second O-ring 59, and thus, it is arranged to prevent the liquid from being leaked to the outside due to such a configuration. At the tip of the tip cap 52, a nozzle hole 71 to be the tip of the liquid flow channel 74 is provided to the nozzle plate 60, and the tip cap 52 sprays the liquid in the spray direction D from the nozzle hole 71 toward an object. Further, by using fluorine-containing rubber, silicon rubber, or EPDM as the material of the second O-ring 59, it is possible to make elution from the second O-ring 59 low.

As described above, the hand piece 42 in the present practical example is provided with the nozzle hole 71 for spraying the liquid toward the object, the liquid flow channel 74 communicated with the nozzle hole 71, and the filter 58 disposed in the liquid flow channel 74. Further, in the hand piece 42 in the present practical example, the filter 58 is formed of an antibacterial member. It is preferable to adopt such a configuration in which at least a part of a liquid flow channel 72 from the filter 58 to the nozzle hole 71 out of the filter 58 and the constituent members in the liquid flow channel 74 forms an antibacterial part as described above.

When at least a part of the filter 58 and the liquid flow channel 72 from the filter 58 to the nozzle hole 71 forms the antibacterial part as in the hand piece 42 in the present practical example, it is possible to prevent the bacterium from propagating in the liquid flow channel 72 in the vicinity of the nozzle hole 71. When it is possible to prevent the bacterium from propagating in the liquid flow channel 72 in the vicinity of the nozzle hole 71, it is possible to prevent the nozzle hole from plugging up to cause the spray failure.

As the configuration in which at least a part of the filter 58 and the liquid flow channel 72 from the filter 58 to the nozzle hole 71 forms the antibacterial part, it is possible to adopt a configuration in which at least a part of the filter 58 is formed of the antibacterial member as the antibacterial part as in the hand piece 42 in the present practical example. By adopting such a configuration, it is possible to prevent the bacterium from propagating in the liquid flow channel 72 in the vicinity of the nozzle hole 71 using the filter 58 as the antibacterial part. It should be noted that, needless to say, the liquid flow channel 72 includes not only a space through which the liquid flows, but also a member constituting that space.

Further, as the configuration in which at least a part of the filter 58 and the liquid flow channel 72 from the filter 58 to the nozzle hole 71 forms the antibacterial part, it is possible to adopt a configuration in which at least a part of the liquid flow channel 72 from the filter 58 to the nozzle hole 71 such as a formation portion of the nozzle hole 71 is formed of the antibacterial member as the antibacterial part. By adopting such a configuration, it is possible to prevent the bacterium from propagating in the liquid flow channel 72 in the vicinity of the nozzle hole 71 using the liquid flow channel 72 as the antibacterial part.

Further, as the configuration in which at least a part of the filter 58 and the liquid flow channel 72 from the filter 58 to the nozzle hole 71 forms the antibacterial part, it is possible to adopt a configuration in which a filter holding section for holding the filter 58 such as the filter holder 61 is provided to the liquid flow channel 74 as in the hand piece 42 in the present practical example, and at least a part of the filter holding section is formed of the antibacterial member as the antibacterial part. By adopting such a configuration, it is possible to prevent the bacterium from propagating in the liquid flow channel 72 in the vicinity of the nozzle hole 71 using the filter holding section as the antibacterial part.

It should be noted that the filter 58 as the antibacterial part in the present practical example is formed of antibacterial resin. It should be noted that the material of the antibacterial member of the antibacterial part is not limited to resin. As the antibacterial member of the antibacterial part, it is possible to use a variety of material such as metal other than resin as long as the material has an antibacterial effect.

Practical Example 2

Figure 8:
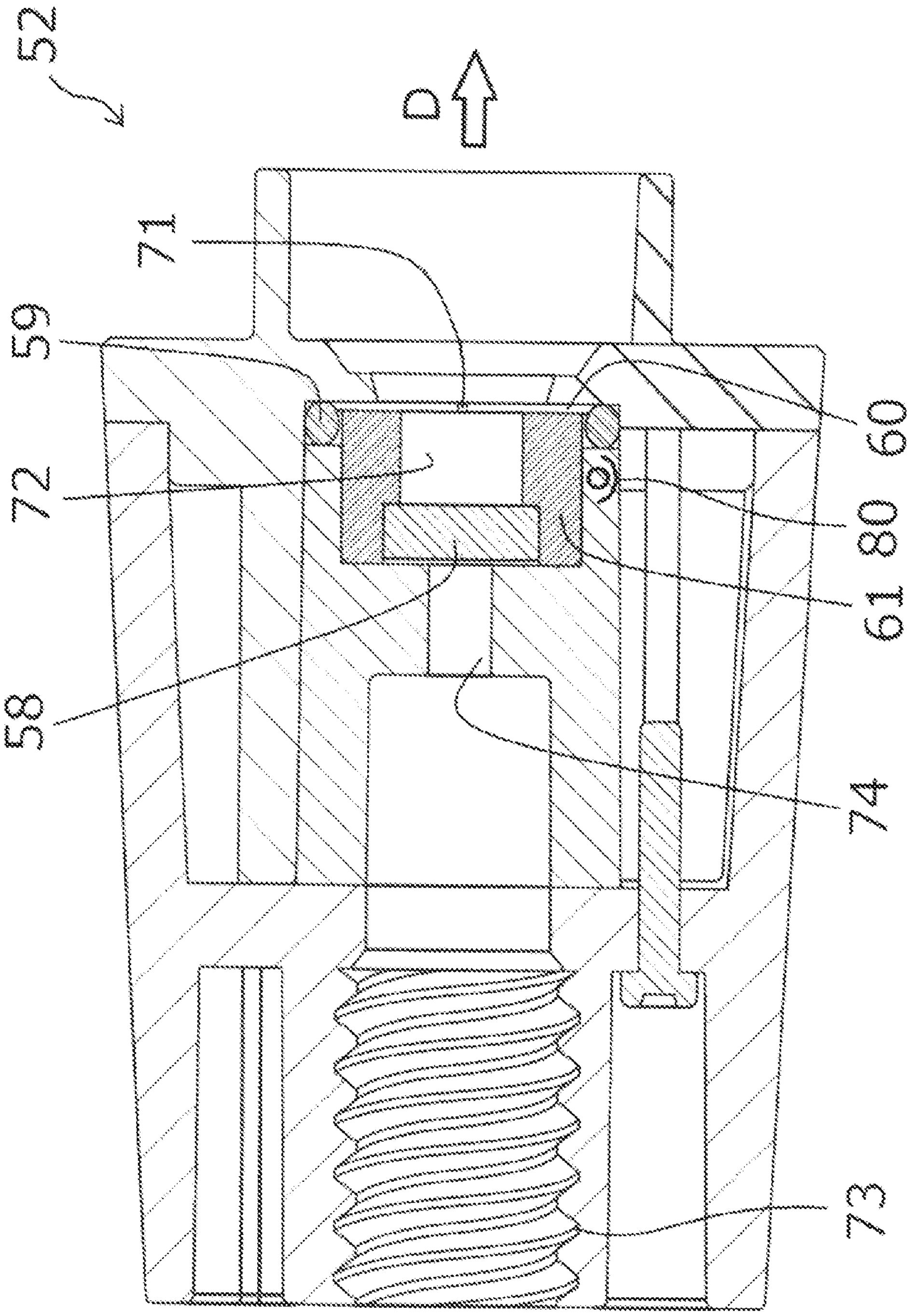
FIG. 8 is a cross-sectional view of a nozzle unit of a liquid spray nozzle according to Practical Example 2 of the present disclosure.

Then, the hand piece 42 in Practical Example 2 will be described with reference to FIG. 8. It should be noted that FIG. 8 is a diagram corresponding to FIG. 7 of the hand piece 42 in Practical Example 1, and in FIG. 8, the constituent members common to the present practical example and Practical Example 1 described above are denoted by the same reference numerals, and the detailed description will be omitted. Here, the hand piece 42 in the present practical example has substantially the same features as those of the hand piece 42 in Practical Example 1 described above, and at the same time, has substantially the same configuration as that of the hand piece 42 in Practical Example 1 except the following descriptions.

As shown in FIG. 8, in the hand piece 42 in the present practical example, there is provided a light emitter 80 for emitting ultraviolet light toward the liquid flow channel 72 as the antibacterial part. Therefore, it is possible for the hand piece 42 in the present practical example to prevent the bacterium from propagating in the liquid flow channel 72 in the vicinity of the nozzle hole 71 using the light emitter 80 as the antibacterial part.

It should be noted that in the hand piece 42 in the present practical example, the filter holder 61 is formed of a material capable of transmitting the ultraviolet light from the light emitter 80.

Practical Example 3

Then, the droplet-impact pressure facial cleanser as the liquid spray device 100 equipped with the hand piece 42 in Practical Example 3 will be described with reference to FIG. 9 through FIG. 16. In FIG. 9 through FIG. 16, constituents common to the present practical example and Practical Example 1 described above are denoted by the same reference numerals, and the detailed description thereof will be omitted.

Figure 9:
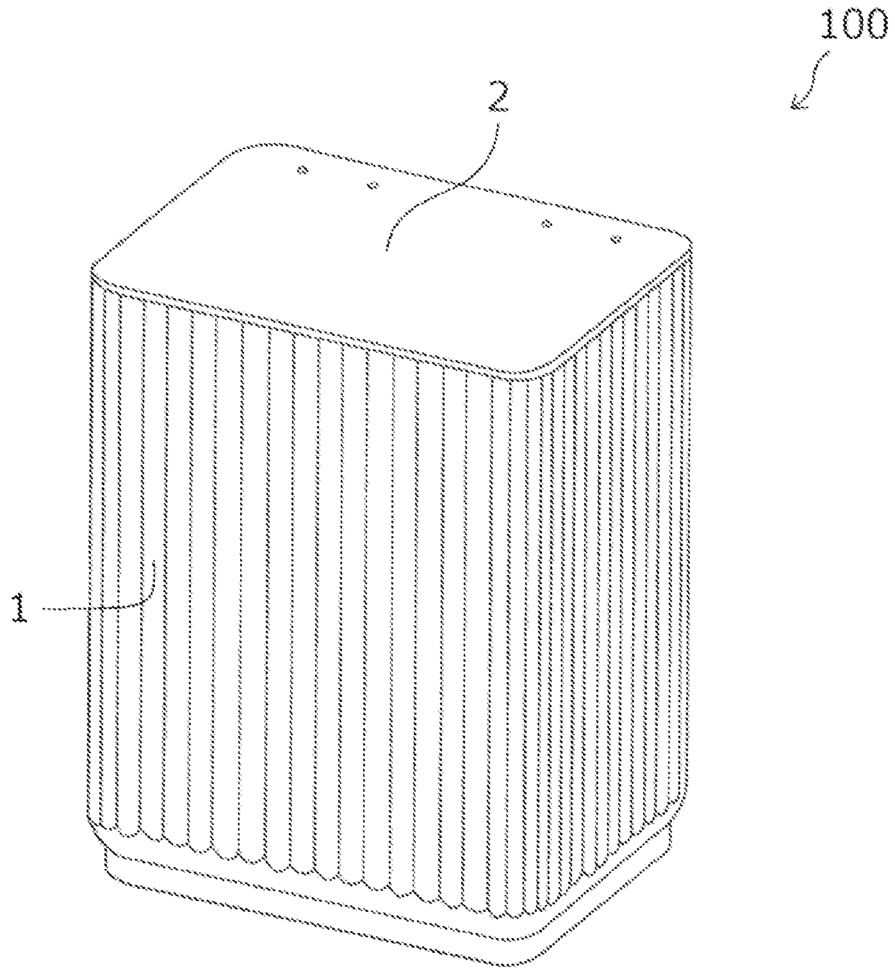
FIG. 9 is a schematic perspective view of the whole of a liquid spray device having a liquid spray nozzle according to Practical Example 3 of the present disclosure, and shows a state in which a lid is closed.

An embodiment of an overall configuration of the droplet-impact pressure facial cleanser equipped with a head having the antibacterial function according to the present application will hereinafter be described. As shown in FIG. 9, an exterior appearance of a main body of the droplet-impact pressure facial cleanser is constituted by the case 1 and the lid 2. The main body in the state in which the lid 2 is closed has a surface state and a size easy to carry, and has an exterior appearance fitting in interior decors such as a living room, a shelf, and a vanity. The lid 2 is arranged to cover the entire area of an upper surface of the case 1 to give consideration so that dust, dirt, and so on during disuse do not enter the main body.

The lid 2 is coupled to the case 1 with a plurality of hinges 3 disposed at a back side. At least one of the hinges 3 is provided with a rotation torque limiting mechanism to give consideration so as to prevent the lid 2 from closing under its own weight to pinch a finger of the user. A locking mechanism for the lid 2 is disposed between the lid 2 and the case 1 to give consideration so that an unintended opening operation of the lid during disuse and so on is not performed. The locking mechanism can be disposed in the vicinity of the hinge 3 or provided to the hinge 3 which couples the lid 2 and the case 1 to each other.

Figure 10:
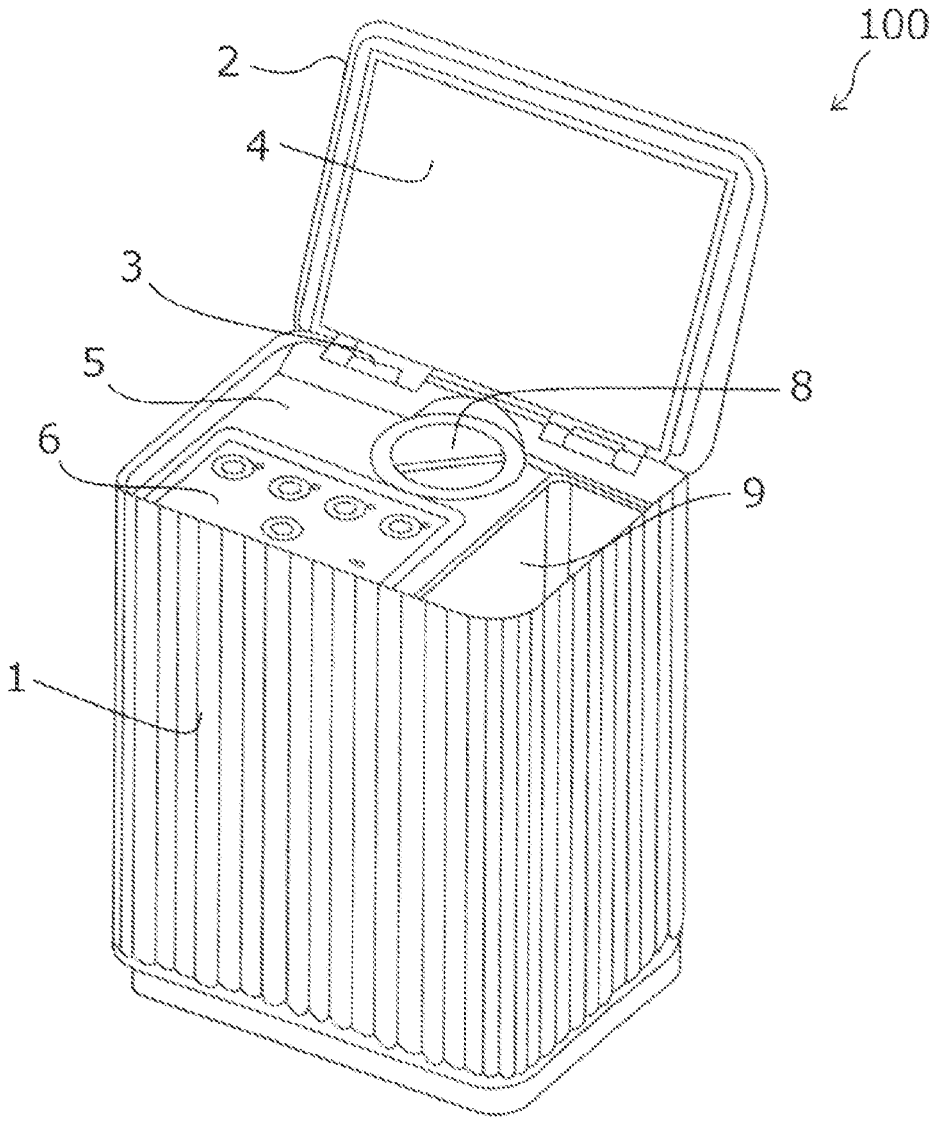
FIG. 10 is a schematic perspective view of the whole of the liquid spray device shown in FIG. 9, and shows a state in which the lid opens.

An inside arrangement and so on when opening the lid 2 will be described using FIG. 10. To a surface located inside the main body of the lid 2 which is opened, there is attached a mirror 4. The mirror 4 is mainly used for showing the state of the skin of the user before the operation, during the operation, and after the operation to the user. As an advanced application example, it is possible to adopt an image display in which an imaging machine having an electronic imaging function is disposed in a lid portion or in the vicinity thereof, and which is capable of displaying an image thus taken, a result of an analysis of the image thus taken, or both thereof.

Further, as another application example, it is possible to provide a structure of holding portable communication equipment (a smartphone) or the like on an edge located at the user side of the lid 2 or in the vicinity thereof. In another proposal, there is proposed a diagnostic imaging system or the like using portable communication equipment, and it is possible to use the structure as a holding mechanism for the present portable communication equipment for the diagnostic imaging system. Further, it is possible for a light source to be arranged in an edge portion of the mirror 4 described above. The light source is used mainly for clearly observing the state of the skin of the user.

Figure 11:
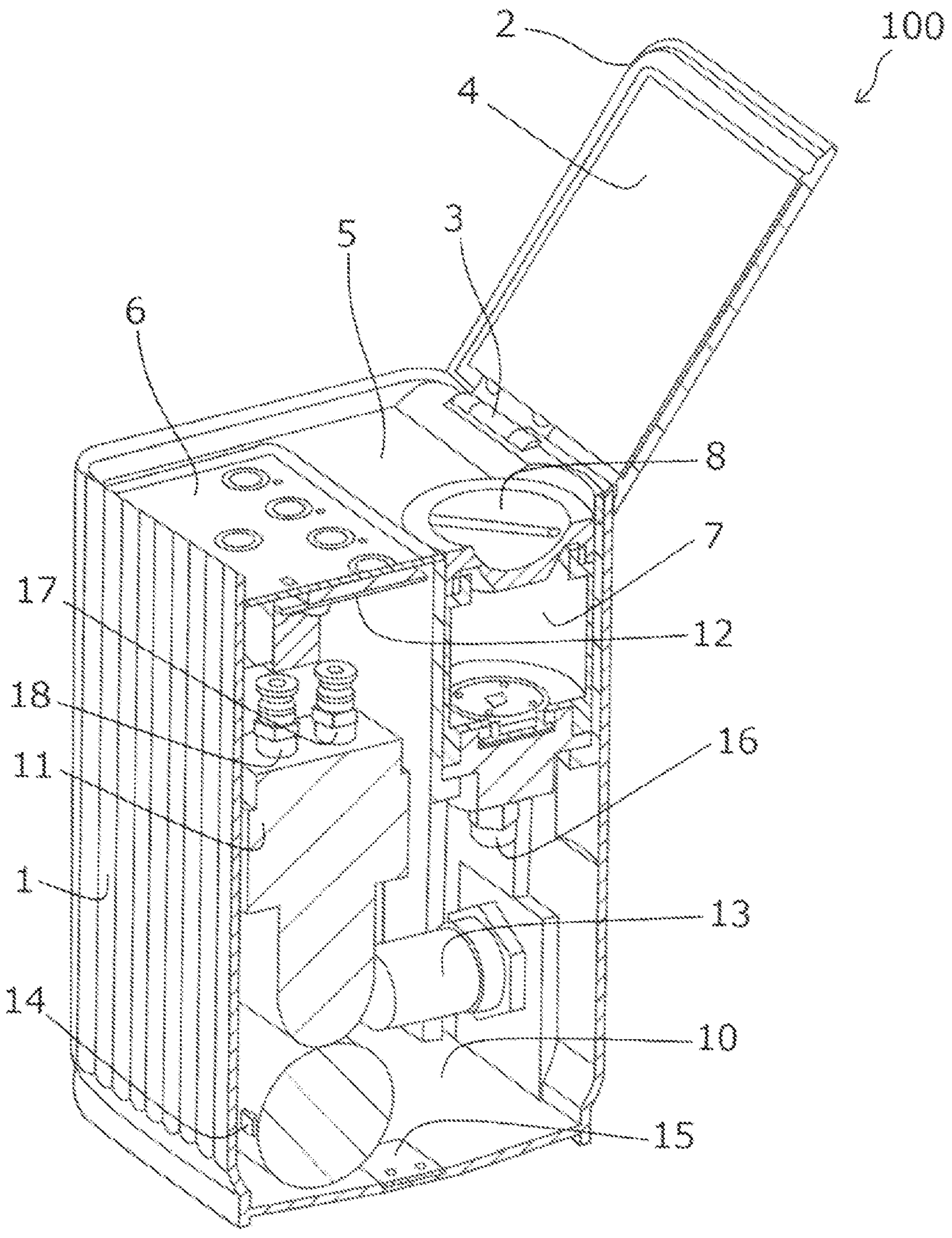
FIG. 11 is a schematic perspective view of the whole of the liquid spray device shown in FIG. 9.

An inside configuration and an outside configuration of the case 1 will be described using FIG. 10 and FIG. 11. On a decorative sheet 5 or in the vicinity thereof, there are arranged at least the operation panel 6 of the present equipment, and the tank 7 for pouring an ejection liquid necessary for a principal function of the equipment, and the tank 7 is provided with the tank lid 8 which can be detached as a function of preventing the dust and the dirt from entering the tank 7. Inside the case 1 in the state in which the lid 2 opens, the hand piece housing section 9 for housing the hand piece 42 is disposed at the right side (or can be disposed at the left side) of the decorative sheet 5. In the case 1, there is disposed a wall surface for partitioning the inside thereof, and thus, the inside of the case 1 is divided into the hand piece housing section 9 and a mechanism-and-so-on inclusion section 10.

The mechanism-and-so-on inclusion section 10 includes a mechanism such as a conveying mechanism of the liquid and electric components. On the wall surface for partitioning the mechanism-and-so-on inclusion section 10 and the hand piece housing section 9 from each other, there is performed an appropriate treatment so that the liquid such as water does not enter the mechanism-and-so-on inclusion section 10 through a combining portion with the case 1. As the appropriate treatment, there can be cited, for example, sealing with a seal member, sealing with a caulking material, and a device on shaping. Substantially the same treatment as performed on the wall surface is also performed between the tank 7 and the decorative sheet 5 to give consideration so that water does not enter the mechanism-and-so-on inclusion section 10 when, for example, the user refills the tank 7 with the liquid. The operation panel 6 is formed of a different member from the decorative sheet 5, and a space between the two members, namely the operation panel 6 and the decorative sheet 5, is tightly sealed with, for example, a waterproof double-sided tape to give consideration so that there is no chance for the liquid to enter the mechanism-and-so-on inclusion section 10. The sealing is not limited to the waterproof double-sided tape, and it is possible to achieve the waterproof function with the sealing member separately prepared.

The mechanism-and-so-on inclusion section 10 will be described using FIG. 11. In the mechanism-and-so-on inclusion section 10, there are housed a pump 11 used for conveying the liquid, a control board 12, a DC jack 13, a thermistor 14 for monitoring the drive source temperature of the pump 11, and a leakage sensor 15 for detecting the liquid having entered the mechanism-and-so-on inclusion section 10. Further, the tank is provided with a tank ejection port 16 for guiding the liquid retained in the tank to the pump, and a liquid return port not shown. It should be noted that it is possible for a bottom surface of the mechanism-and-so-on inclusion section 10 to be provided with a discharge port for discharging the liquid which has entered the mechanism-and-so-on inclusion section 10.

Functions of the respective elements housed therein will hereinafter be described. The pump 11 has a function of conveying the liquid. The pump 11 is provided with a pump feed port 17, a pump ejection port 18, and a return liquid ejection port which is not shown. The pump 11 is provided with a piston type mechanism which can be small in size and high in ejection power, and is equipped with a motor driven with DC power as a drive source of the liquid conveyance. It should be noted that a diaphragm type mechanism can be used as the mechanism of the pump 11 instead of the piston type mechanism. Further, the thermistor 14 for detecting the temperature of the motor when the motor is overheated is attached to an outer wall of the motor or the vicinity thereof with an arranging bracket. The thermistor 14 can be screwed together with the motor using fixing screws for the motor. The thermistor 14 is electrically coupled to the control board 12 described above, and a pump stop function installed in the control board 12 is activated when the temperature of the motor exceeds a predetermined value.

A function of the leakage sensor 15 will be described. A detection part of the leakage sensor 15 is arranged below all of energized parts included in the mechanism-and-so-on inclusion section 10 with reference to a gravitational direction. The leakage sensor 15 is electrically coupled to the control board 12, and transmits the fact that the liquid having electrical conductivity has entered the mechanism-and-so-on inclusion section 10 from the outside thereof to the control board 12 when the fact has occurred. The control board 12 cuts off the power using an interlock mechanism provided to the DC jack 13. Alternatively, the control board 12 can perform an operation of receiving signals from the thermistor 14 and the leakage sensor 15, then stopping the power supply to the motor, and at the same time, making display equipment operate in order to transmit the fact to the user.

A flow channel configuration of the pump 11 will be described. The pump feed port 17 is coupled to the tank ejection port 16 via, for example, a PVC tube having flexibility. The return liquid ejection port of the pump described above is coupled to the liquid return port described above via, for example, a PVC tube having flexibility. To the pump ejection port 18, there is coupled, for example, a PVC tube having flexibility, and the PVC tube or the like passes a hole part provided to the wall surface provided between the mechanism-and-so-on inclusion section 10 and the hand piece housing section 9, and is guided to the hand piece housing section 9. A consideration of preventing the liquid from inflowing into the mechanism-and-so-on inclusion section 10 from the hand piece housing section 9 with a grommet or some sealing material is given to the hole part.

The pump 11 is fixed to any one or a plurality of members such as the inside of the case 1, the wall surface described above, and the decorative sheet 5, and is fixed via the an antivibration mechanism so that the vibration generated by the pump does not become a noise. The most common structure as the antivibration mechanism is to use a vibration isolating material, but it is possible to use a mechanism having elasticity such as a spring. The function required to be achieved here is to provide a structure in which a rigid portion of the pump 11 does not make direct contact with the case 1, the wall surface, and the decorative sheet 5. In order to realize the above, a vibration isolating material and an attaching bracket not shown are arranged between the case 1 and the pump 11.

The drive power to the motor installed in the pump 11 is supplied from the control board 12. The DC jack 13 is installed in the case 1, a power line of an AC adapter or the like is coupled to the DC jack 13 from the outside, and the power is supplied from an external power supply. On an outer surface of the case 1 in the DC jack 13, there is installed a DC jack lid not shown having water-proof function so as to prevent the DC jack 13 from getting wet with water during disuse. The power input to the DC jack 13 is electrically coupled to the control board 12.

The control board 12 will be described. Although partially overlapping the above description, the description is presented in order to make the explanation easy. The control substrate 12 is divided into two main parts. One is an operation section, and another is a control section 31. The operation section is provided with a power button, and at least one operation selection button for the user to select a desired operation mode. These buttons are coupled to the control section 31 to define a variety of operations.

In the control section 31, there are provided a driving driver for driving at least the pump 11, an operation portion for controlling a drive situation to the pump 11 in accordance with selection of a use mode, and a coupling part to which the thermistor 14, the leakage sensor 15, and the power from the DC jack 13 are coupled. The control section 31 performs operation stoppage of the pump 11 due to signals from at least the thermistor and the leakage sensor 15. Further, there is provided an arithmetic function of performing power shutdown in the DC jack 13.

Switching of the operation mode, switching of flow power, and so on are arranged to be performed by operating the operation panel 6 provided to the decorative sheet 5. In the operation panel 6, there is set an operation mode corresponding to each nozzle plate, and in each of the operation modes, there are set a flow rate (a rotational frequency of the motor installed in the pump 11) and rotation time (spray time) of the motor.

It should be noted that by using a more simple description such as a picture instead of characters as information to be displayed on the operation panel 6, the operation becomes easy to perform. Further, the operation panel 6 is arranged so that it is possible to confirm what operation mode is selected, and a display section of the operation mode can be formed using, for example, an LED element and a light guide member. It should be noted that the confirmation of the operation mode is not limited to the method described above, and it is possible to arrange to give notice with, for example, a sound.

Figure 12:
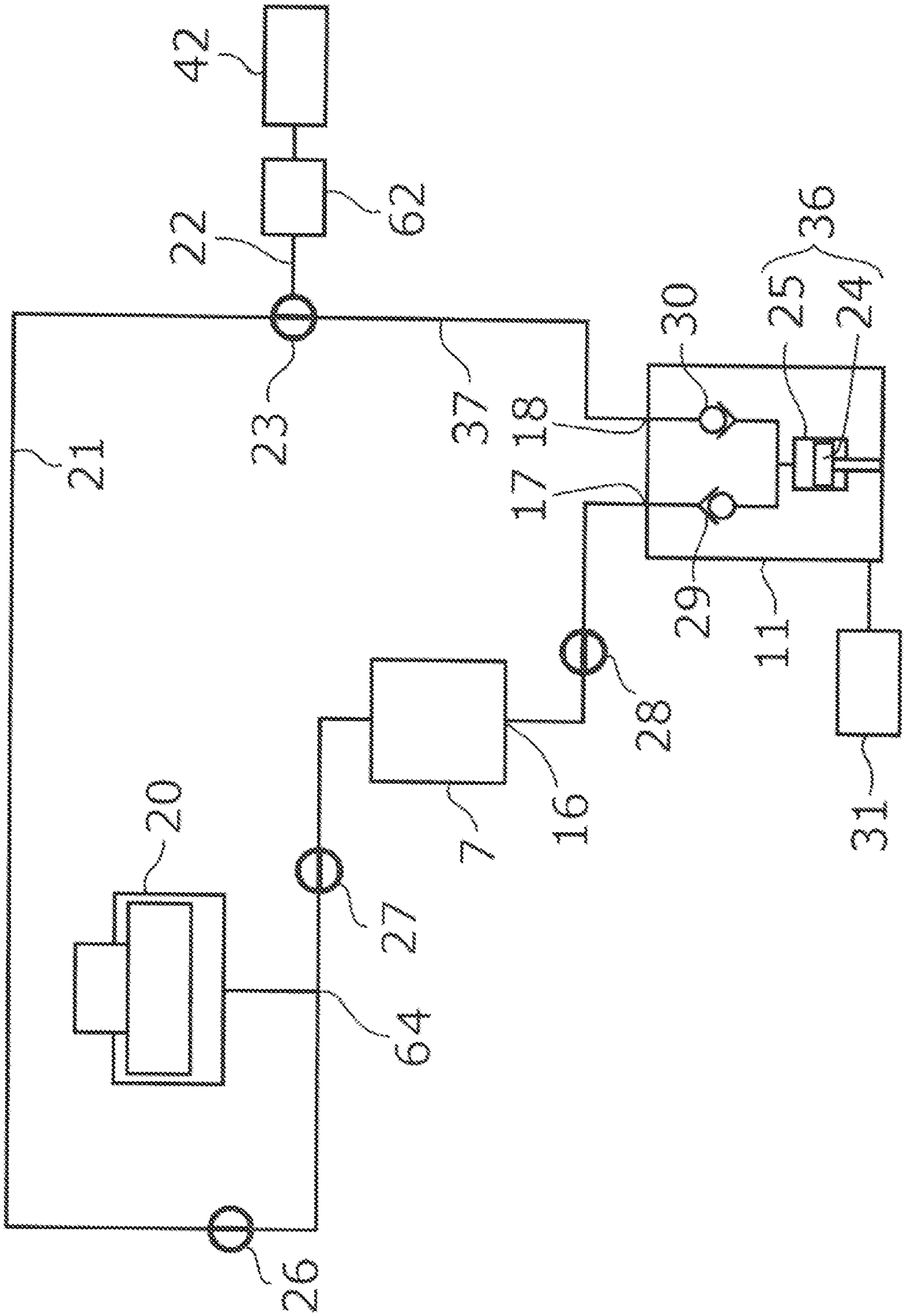
FIG. 12 is an explanatory diagram of a configuration of a first system of a conveying channel of a liquid applicable to the liquid spray device shown in FIG. 9.

As the configuration of a conveying channel of the liquid, a plurality of systems described below can be applied. FIG. 12 shows a configuration example of a first system of the conveying channel. When a movable part 20 is disposed so as to be blanched from a circulation channel 21 disposed from the downstream of the pump ejection port 18 via a blanch part, a first valve 23 which performs opening or blocking with a spray channel 22, a second valve 26 which is a constituent capable of making the spray liquid flow together with bubbles to the circulation channel 21 due to an operation of the first valve 23 to return to the tank 7, and performs opening or blocking of a channel disposed between the first valve 23 and the circulation channel 21 and the movable part 20, a third valve 27 which performs opening and blocking of a channel disposed between the tank 7 and a coupling part 64, and a fourth valve 28 which performs opening and blocking of a channel disposed between the pump 11 and the tank 7 are disposed, and the control section 31 is provided with a protocol instruction function when performing switching of the valves, when the channel is depressurized using the opening or blocking operation of the channel and the operation of the movable section 20 to thereby expand the gas in a place to facilitate the gas to be discharged, and for example, the inside of the pump 11 is constituted by a pressurizing section 36 formed of a piston 24 and a cylinder 25, a feed check valve 29, and an ejection check valve 30, in a state in which bubbles adhere to a corner part and so on of the cylinder 25, and thus, the bubbles cannot be moved by the normal liquid delivery drive, and thus, the pressurization of the liquid by the piston cannot sufficiently be achieved, it is possible to discharge the bubbles to the outside of the pressurizing section to achieve stable filling with the spray liquid and the bubble discharge in the liquid delivery channel 37. The spray channel 22 is provided with a pressure detection section 63 and the hand piece 42. It should be noted that the switching operation of the valves is not limited to the operation in accordance with the protocol instruction by the control section, and can also be realized by substantially the same manual operation. Further, the inside of the pump 11 can be constituted by a plurality of pressurizing sections 36, the feed check valve 29, and the ejection check valve 30, and the same applies to a pressurizing mechanism constituted by a diaphragm and a reciprocal motion of a bellows.

Figure 13:
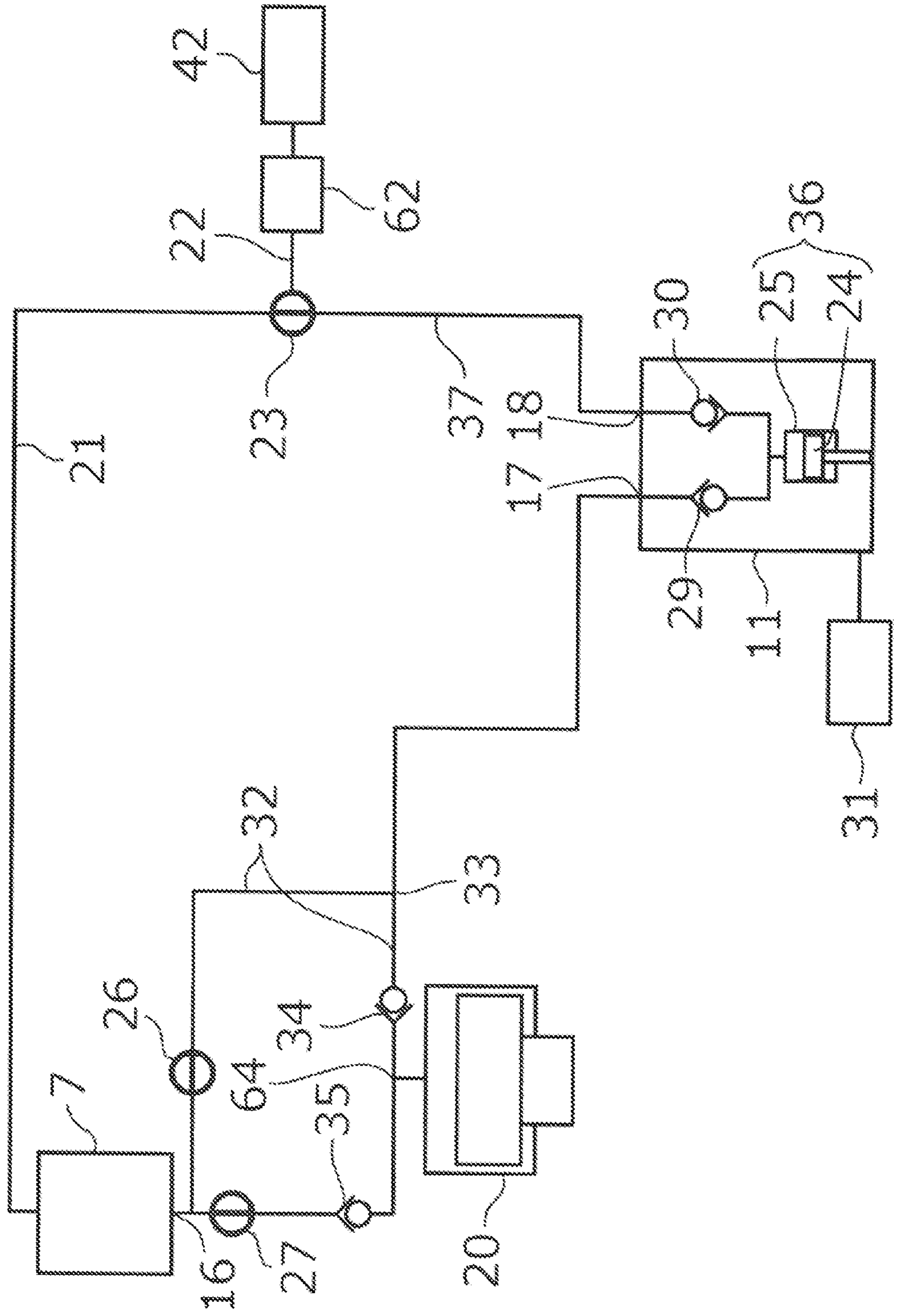
FIG. 13 is an explanatory diagram of a configuration of a second system of the conveying channel of the liquid applicable to the liquid spray device shown in FIG. 9.

FIG. 13 shows a configuration example of a second system of the conveying channel. In the configuration in which the movable section 20 capable of performing a push-pull operation, and capable of delivering the spray liquid to the pump 11 and the inside of the device is coupled so as to be blanched from the coupling part 64 located on a blanch channel 32 branched at the upstream of the pump feed port 17 and at the downstream of the tank ejection port 16, and a second check valve 35 disposed between the coupling part 64 and the tank 7, and a first check valve 34 disposed between a branch point 33 and the coupling part 64 are provided, when the inside of the pump 11 is constituted by, for example, the pressurizing section 36 formed of the piston 24 and the cylinder 25, the feed check valve 29, and the ejection check valve 30 similarly to the first system, in the state in which the bubbles are in a state of adhering to the corner part and so on of the cylinder 25, and thus, cannot be moved by the normal liquid delivery drive, and thus, the piston cannot sufficiently pressurize the liquid, by pressurizing or depressurizing the inside of the channel due to the operation of the movable section 20 to make the spray liquid flow together with the bubbles, it is possible to discharge the bubbles to the outside of the pressurizing section 36 to achieve stable filling with the spray liquid and the bubble discharge in the liquid delivery channel 37.

Further, in the configuration of the conveying channel shown in FIG. 13, the branch channel 32 has the second valve 26 for performing opening or blocking of the channel and the third valve 27 in addition to a branch which is branched from the tank 7 and delivers the spray liquid to the pump 11 without intervention of the coupling part 64 and the movable section 20, and the control section 31 is provided with the protocol instruction function when performing the switching of the valves, by performing the valve switching so that there is established the state of delivering the spray liquid to the pump 11 without intervention of the coupling part 64 and the movable section 20 described above after the discharge of the gas by the drive of the movable section 20 is completed, it is possible to decrease a suction resistance of the pump after the filling with the spray liquid, and thus, it becomes possible to perform driving in the state in which the suction load of the pump 11 is reduced. Although the pump 11 is not particularly limited, it is possible to preferably use, for example, a liquid delivery pump system which is produced by TENRYUMARUSAWA Co., Ltd., and which has a configuration of the pump 11, the movable section 20, and the branch channel 32. Further, when the suction resistance load to the pump 11 is negligible, an operation can be performed with a configuration of delivering the spray liquid to the pump 11 via the coupling part 64 and the movable section 20 without using the valve switching after discharging the bubbles in the pressurizing section 36.

Figure 14:
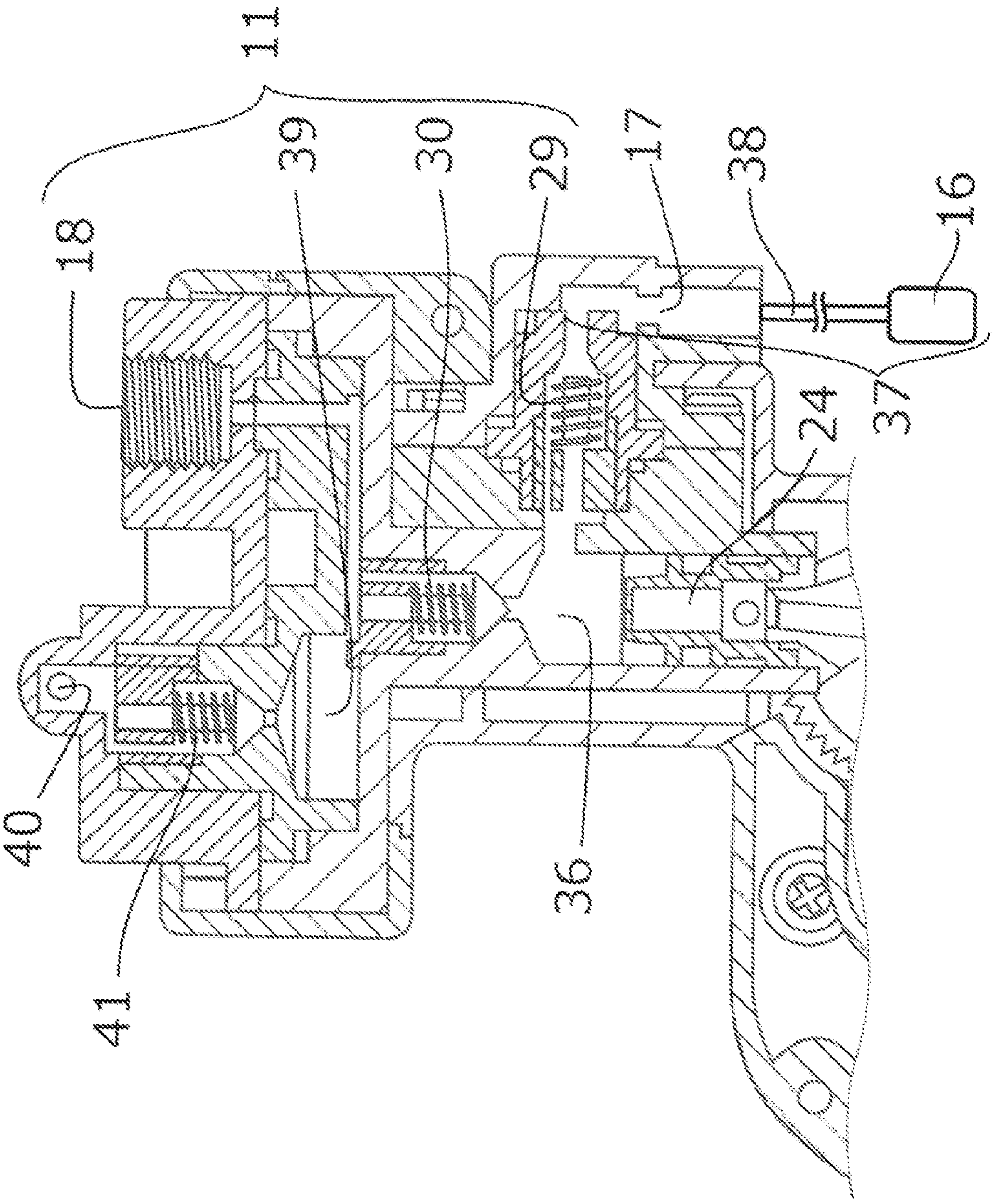
FIG. 14 is an explanatory diagram of a configuration of a third system of the conveying channel of the liquid applicable to the liquid spray device shown in FIG. 9.

FIG. 14 shows a configuration example of a third system of the conveying channel. The pump 11 is not particularly limited, but it is preferable for the pump 11 to perform self-suction even under the condition in which the flow channel resistance at the ejection port side is high. It is possible to eject the gas existing in the pump 11, in particular in the pressurizing section 36, to perform filling with the spray liquid only by driving the pump 11. For example, as the pump 11, it is preferable to use the pump 11 provided with a space (an air pocket 39) having substantially the same volume as a total volume (the pressurizing section 36, the pump feed port 17, the feed check valve 29, and a feed channel 38) of the liquid delivery channel 37 between the pressurizing section 36 and the tank ejection port 16 at the downstream of the ejection check valve 30 released by the pressurization of the pressurizing section 36 of the pump produced by TENRYUMARUSAWA Co., Ltd., and a bubble discharge valve 41 which does not transmit the spray liquid to a return liquid ejection port 40 side until the bubble discharge valve 41 is pressed with a constant force such as a spring force to be opened, in which a contact of a component for closing the channel is thin (point contact). Here, the bubble discharge valve 41 is set to be opened with a stronger force than the opening force of the ejection check valve 30, and when the pressure at the downstream of the pressurizing section 36 exceeds the predetermined pressure, the spring force becomes inferior to the pressure, and thus, the bubble discharge valve 41 is opened, and therefore, has the function as a safety valve.

Figure 15:
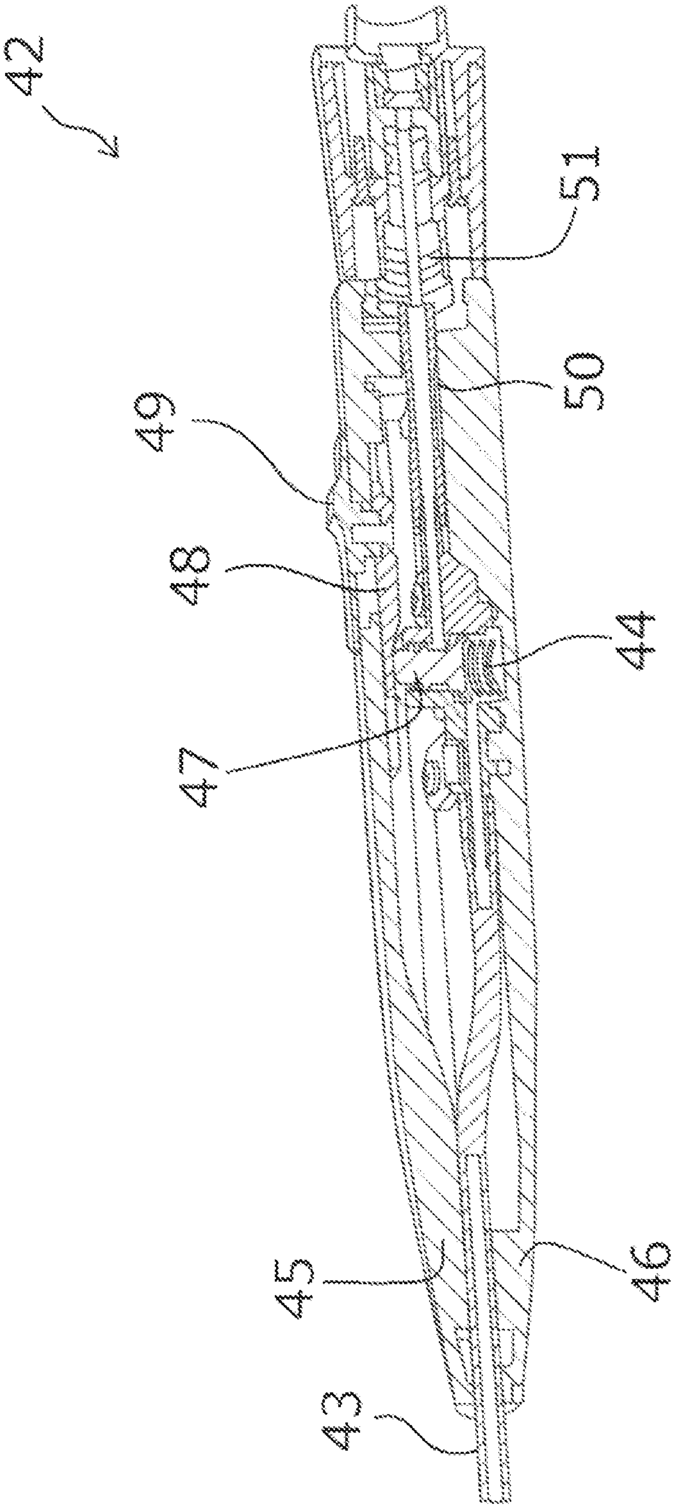
FIG. 15 is a cross-sectional view of a liquid spray nozzle according to Practical Example 3 of the present disclosure.
Figure 16:
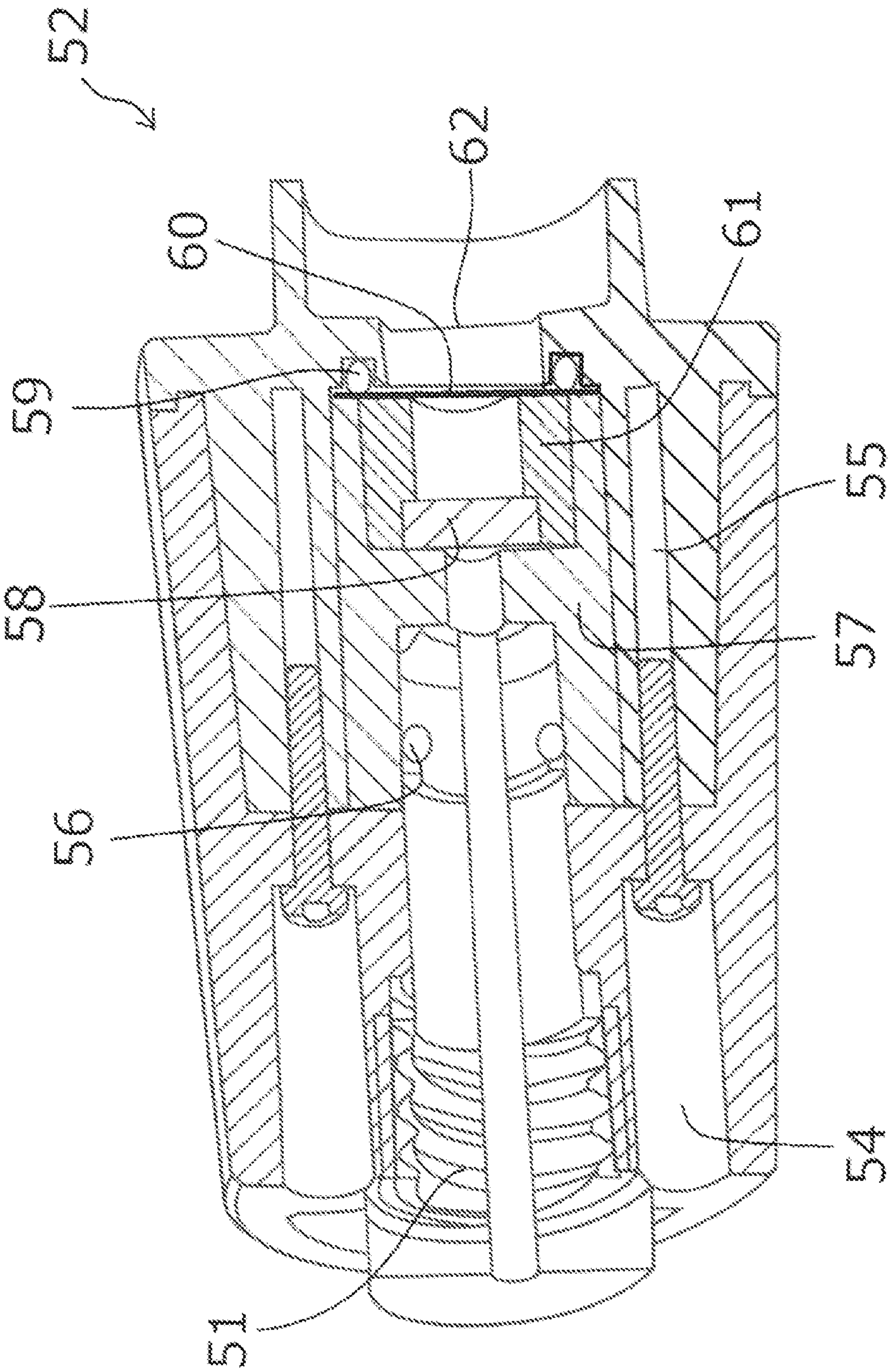
FIG. 16 is a cross-sectional view of a nozzle unit of the liquid spray nozzle according to Practical Example 3 of the present disclosure.

A structure and a function of the hand piece 42 in the present practical example will be described using FIG. 15 and FIG. 16. The liquid delivery tube 43 extracted through the wall surface from the mechanism-and-so-on inclusion section 10 is guided to the inside of the hand piece 42. The liquid delivery tube 43 is coupled to an inflow port of the valve ASSY 44 installed in the hand piece 42. Further, the liquid delivery tube 43 is held by narrowed areas which are not shown, and are provided to an upper case 45 and a lower case 46, and there is given a consideration that when a pulling force is applied to the liquid delivery tube 43, an increase in the pull-out force is achieved.

The valve ASSY 44 is provided with a valve rod 47, and has a function of switching between blocking and opening of a channel between the inflow port and the outflow port in accordance with the position of the valve rod 47. Below the valve rod 47, there is disposed a spring, and the channel is blocked when no pressing force is applied, and the channel opens when the pressing force is applied. The valve rod 47 is pressed by a sliding plate 48 provided to the upper case 45, and the valve opening and closing switch 49, and the arrangement change for blocking or opening is made.

To an ejection port provided to the valve ASSY 44, there is coupled the coupling tube 50, and the coupling tube 50 is coupled to the tip cap connector 51. The tip cap connector 51 is provided with a screw structure in a coupling fixation portion to the tip cap 52, and there is formed a structure in which the tip cap 52 can be fixed with a screwing action. A first O-ring 56 is installed in the tip cap connector 51 to prevent the liquid from being leaked from a joint part with the tip cap 52.

The tip cap 52 houses a first tip cap part 54, a second tip cap part 55, the first O-ring 56, an inner cap 57, the filter 58, the second O-ring 59, the nozzle plate 60, and the filter holder 61, and the first tip cap part 54 and the second tip cap part 55 are screwed to each other to thereby be integrated with each other. The filter 58 is coupled to the filter holder 61 and the inner cap 57, and is pressed against the inner cap 57 with the filter holder 61 compressed by the nozzle plate 60. Due to the reactive force caused by the compression of the filter holder 61, the filter holder 61 presses the filter 58 against the inner cap 57, and at the same time, presses the liquid spray nozzle against an inner wall of the second tip cap part 55. Here, the filter 58 is arranged to be able to prevent a foreign matter from flowing into the nozzle plate 60 to cause clogging, and both of a net-like metal filter and a membrane filter can be applied as the filter 58. Further, the filter 58 is detachably attached to the second tip cap part 55, and can be detached to clean the filter 58. It should be noted that it is possible to integrate the filter 58 and the second tip cap part 55 with each other, and it is also possible to adopt a double filter configuration.

Between the nozzle plate 60 and the second tip cap part 55, there is disposed the second O-ring 59, and thus, the liquid is prevented from being leaked from a gap caused between the second tip cap part 55 and the nozzle plate 60. It should be noted that it is preferable to use a material difficult for an impurity to elute due to physical or chemical functioning with the liquid flowing such as a fluorinated material for the first O-ring 56 and the second O-ring 59 to thereby prevent clogging of the nozzle plate 60.

The nozzle plate 60 is provided with microscopic ejection openings, and there is a concern that damage due to an impact from the outside occurs in the microscopic ejection openings described above when handling the hand piece 42. In order to prevent the above, the second tip cap part 55 is provided with a jet ejection part 62 having a protrusion. It should be noted that the nozzle plate 60 is provided with a plurality of ejection openings. A diameter φ of the ejection opening is in a range of 0.01 mm through 0.03 mm, which is smaller than a diameter of a typical pore in a range of 0.2 mm through 0.4 mm, and therefore, it becomes easy for the liquid (droplets) ejected from the ejection opening to enter the pores, and therefore, it is possible to more efficiently wash away the dirt in the pores.

The present disclosure is not limited to the practical examples described above, but can be implemented with a variety of configurations within the scope or the spirit of the present disclosure. The technical features in the practical examples corresponding to the technical features in the aspects described in SUMMARY section can appropriately be replaced or combined in order to solve all or a part of the problems described above, or in order to achieve all or a part of the advantages. Further, the technical feature can arbitrarily be eliminated unless described in the present specification as an essential element.

What is claimed is:

1. A liquid spray nozzle comprising:

a nozzle hole configured to spray a liquid toward an object;

a liquid flow channel communicated with the nozzle hole;

a filter disposed in the liquid flow channel, wherein at least one of a part of the filter and a part of the liquid flow channel from the filter to the nozzle hole forms an antibacterial part; and a filter holding part configured to hold the filter in the liquid flow channel, wherein at least a part of the filter holding part is formed of an antibacterial member as the antibacterial part.

2. The liquid spray nozzle according to claim 1, wherein at least the part of the filter is formed of an antibacterial member as the antibacterial part.

3. A liquid spray device comprising:

the liquid spray nozzle according to claim 2; and a liquid supply device configured to supply the liquid spray nozzle with the liquid.

4. The liquid spray nozzle according to claim 1, wherein at least the part of the liquid flow channel from the filter to the nozzle hole is formed of an antibacterial member as the antibacterial part.

5. A liquid spray device comprising:

the liquid spray nozzle according to claim 4; and a liquid supply device configured to supply the liquid spray nozzle with the liquid.

6. A liquid spray device comprising:

the liquid spray nozzle according to claim 1; and a liquid supply device configured to supply the liquid spray nozzle with the liquid.

* * * * *